United States Patent [19]

Grosselin

[11] Patent Number: 5,003,110
[45] Date of Patent: Mar. 26, 1991

[54] PROCESS FOR THE PREPARATION OF SATURATED ALDEHYDES BY HYDROGENATION OF α,β-UNSATURATED ALDEHYDES

[75] Inventor: Jean-Michel Grosselin, Lyons, France

[73] Assignee: Rhone-Poulenc Sante, Antony, France

[21] Appl. No.: 411,888

[22] Filed: Sep. 25, 1989

[30] Foreign Application Priority Data

Sep. 26, 1988 [FR] France ............................. 88 12521

[51] Int. Cl.$^5$ ............................................. C07C 45/62
[52] U.S. Cl. ..................................... 568/434; 568/462
[58] Field of Search ................................ 568/462, 434

[56] References Cited

U.S. PATENT DOCUMENTS 3,480,659  11/1959  Dewhirst ........................... 568/462
3,639,439  2/1972  Dewhirst ........................... 568/462

FOREIGN PATENT DOCUMENTS 916119  1/1963  United Kingdom ............... 568/462

OTHER PUBLICATIONS

Rylander Engelhard, "Engelhard Industries, Tech. Bull.,", vol. 4, pp. 49–51, Jun. 1963.

Primary Examiner—Werren B. Lone
Attorney, Agent, or Firm—Morgan & Finnegan

[57] ABSTRACT

Saturated aldehydes are prepared by hydrogenation of α,β-unsaturated aldehydes in a two-phase medium in the presence of a catalyst consisting of a rhodium derivative combined with a water-soluble ligand or of a rhodium complex with a water-soluble ligand.

12 Claims, No Drawings

PROCESS FOR THE PREPARATION OF SATURATED ALDEHYDES BY HYDROGENATION OF α,β-UNSATURATED ALDEHYDES

FIELD OF THE INVENTION

The present invention provides a process for the preparation of saturated aldehydes by hydrogenation of α,β-unsaturated aldehydes.

BACKGROUND OF THE INVENTION

Jardine et al, (J. Chem. Soc (C), 270 (1967)) have described the preparation of saturated aldehydes by hydrogenation of unsaturated aldehydes, using tris(triphenylphosphine)chlororhodium. However, to promote the hydrogenation while minimizing the risk of decarbonylation, dilute solutions of the unsaturated aldehyde must be employed, and this makes it difficult to isolate the reaction product or to operate at a high hydrogen pressure. This leads to the formation of a large quantity of the corresponding saturated alcohol.

It is also known, according to C. Larpent et al., (Tetrahedron Letters, 28 (22) 2507 (1987)), to hydrogenate olefins in an aqueous two-phase medium, using rhodium complexes with water-soluble ligands such as tri(-metasulphophenyl)phosphine (TPPTS) as a catalyst, it being possible for the olefins to be functionally substituted by groups which are difficult to reduce such as ketone or acid functional groups.

DETAILED DESCRIPTION OF THE INVENTION

The present invention without limiting it provides a process for the preparation of a saturated aliphatic or araliphatic aldehyde which comprises hydrogenating an α,β-unsaturated aldehyde in a two-phase medium consisting of an organic phase containing said unsaturated aldehyde and an immiscible essentially aqueous phase containing, as catalyst, a rhodium derivative combined with a water-soluble ligand or a rhodium complex with a water-soluble ligand.

The water-soluble ligand is preferably a water-soluble phosphine such as one of those described in French Patent FR 76/22,824 (2,366,237). Tri(meta-sulphophenyl) phosphine (TPPTS) is a particularly preferred ligand.

The rhodium derivatives which are particularly suitable are inorganic or organic salts and complexes of rhodium such as, for example, $RhCl_3$, $RhBr_3$, $Rh_2O$, $Rh_2O_3$, $Rh(NO_3)$, $Rh(CH_3COO)_3$, $Rh(CH_3COCHCOCH_3)_3$, $[RhCl(1,5-cyclooctadiene)]_2$, $[RhCl(CO)_2]_2$ or $RhCl_3(C_2H_5NH_2)_3$. $[RhCl(1,5-cyclooctadiene)]_2$ is a preferred derivative. It is particularly preferable to employ a catalyst of $[RhCl(1,5-cyclooctadiene)]_2$ in combination with (TPPTS).

The reaction is generally carried out in water, with the α,β-unsaturated aldehyde and the saturated aldehyde forming the organic phase. It is possible, however, to perform the process of the invention in the presence of an organic solvent for the aldehyde starting material.

The organic solvents which are particularly suitable are solvents which are immiscible or relatively poorly miscible with water. More particularly, solvents such as alcohols (isopropanol), ethers (ethyl ether, tert-butyl ether), ketones (methyl isobutyl ketone), esters (methyl acetate, ethyl acetate, butyl acetate) and optionally halogenated aliphatic or aromatic hydrocarbons (hexane, toluene, methylene chloride, chloroform, chlorobenzene) may be employed, either individually or as a mixture.

The hydrogenation may be carried out at a temperature of from 0 to 200° C., preferably from 10 to 100° C., and at a pressure of from 1 to 100 bars, preferably from 10 to 50 bars.

Up to 0.05 moles preferably about 0.01 of rhodium derivative are generally employed per mole of α,β-unsaturated aldehyde.

1 to 100 moles of ligand relative to the rhodium are generally employed.

Since the catalyst or the catalyst system is water-soluble, it can be easily separated by phase separation at the end of reaction, and it can thus be recycled.

The process of the invention makes it possible to prepare saturated aliphatic or araliphatic aldehydes from optionally polyunsaturated α,β-unsaturated aliphatic or araliphatic aldehydes. The saturated aldehydes can be obtained with a selectivity which is generally greater than 90%.

The following examples illustrate the invention.

EXAMPLE 1

Rhodium ($5 \times 10^{-4}$ gram-atoms) in the form of $[RhCl(1,5-cyclooctadiene)]_2$, TPPTS ($2 \times 10^{-3}$ moles), hexane (5 cc), water (5 cc) and crotonaldehyde ($24 \times 10^{-3}$ moles) are introduced successively into a 25-cc glass ampoule.

The ampoule is introduced into a 125-cc autoclave, which is placed in an enclosure permitting shaking agitation. The system is purged with hydrogen before the pressure is brought up to 20 bars. The temperature is fixed at 30° C.

After 20 minutes, analysis of the reaction mixture by gas phase chromatography shows that:

the degree of conversion of crotonaldehyde is 88.7% the distribution of the hydrogenation products is the following:
butenol: 1.3%
butanol: 1.8%
butanal 85%
the yield of butanal is 95.6% based on the crotonaldehyde used.

The organic phase is separated by phase separation and hexane (5 cc) and crotonaldehyde ($24 \times 10^{-3}$ moles) are then added to the aqueous phase. When operating in the same temperature and pressure conditions as before, analysis of the reaction mixture after 20 minutes' hydrogenation shows that:

the degree of conversion of crotonaldehyde is 94% the yield of butanal is 97.5% relative to the crotonaldehyde converted.

EXAMPLE 2

Rhodium ($5 \times 10^{-4}$ gram-atoms) in the form of $[RhCl(1,5-cyclooctadiene)]_2$, TPPTS ($2 \times 10^{-3}$ moles), then water (5 cc) and toluene (5 cc) are introduced successively into a 25-cc glass ampoule. 2-Butenal ($2 \times 10^{-2}$ moles) is then added. The ampoule is introduced into a 125-cc autoclave agitated by shaking.

The system is purged with hydrogen. After the hydrogen pressure has been set at 20 bars and the temperature at 40° C., hydrogenation is carried out for 20 minutes.

The reaction mixture is analyzed by gas phase chromatography.

Butanal is thus obtained in a 96% yield relative to the 2-butenal converted.

EXAMPLE 3

The procedure is as in Example 2, 2-butenal being replaced by 3-methyl-2-butenal ($2\times10^{-2}$ moles) and the hydrogenation being carried out at a pressure of 20 bars at 80° C.

3-Methylbutanal is thus obtained in a 96% yield relative to the 3-methyl-2-butenal converted.

EXAMPLE 4

The procedure is as in Example 2, 2-butenal being replaced by cinnamaldehyde ($2\times10^{-2}$ moles) and the hydrogenation being carried out at a pressure of 20 bars at 80° C.

3-Phenylpropanal is thus obtained in a 94% yield relative to the cinnamaldehyde converted.

EXAMPLE 5

The procedure is as in Example 2, 2-butenal being replaced by citral ($2\times10^{-2}$ moles) and the hydrogenation being carried out at a pressure of 40 bars at 60° C.

3,7-Dimethyloctanal is thus obtained in a 96% yield relative to the citral converted.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. A process for the preparation of a saturated aliphatic or araliphatic aldehyde which comprises hydrogenating with hydrogen, at a temperature of from 0° to 200° C. and at a pressure of from 1 to 100 bars, an $\alpha,\beta$-unsaturated aliphatic or araliphatic aldehyde in a two-phase medium consisting of an organic phase containing said unsaturated aldehyde and an immiscible essentially aqueous phase containing as catalyst, a rhodium derivative combined with a water-soluble ligand or a rhodium complex with a water-soluble ligand.

2. A process according to claim 1, wherein the rhodium derivative combined with the water-soluble ligand is an inorganic or organic salt or complex of rhodium.

3. A process according to claim 1, wherein the rhodium derivative combined with the water-soluble ligand is $RhCl_3$, $RhBr_3$, $Rh_2O$, $Rh_2O_3$, $Rh(NO_3)_3$, $Rh(CH_3COO)_3$, $Rh(CH_3COCHOOCH_3)_3$, $[RhCl(1,5\text{-cyclooctadiene})]_2$, $[RhCl(CO)_2]_2$ or $RhCl_3(C_2H_5NH_2)_3$.

4. A process according to claim 1, wherein the water-soluble ligand is a water-soluble phosphine.

5. A process according to claim 4, wherein the water-soluble phosphine is a sulphonated phenylphosphine.

6. A process according to claim 5, wherein the sulphonated phenylphosphine is tri(meta-sulphophenyl)-phosphine.

7. A process according to claim 1 wherein the catalyst employed is $[RhCl(1,5\text{-cyclooctadiene})]_2$ combined with tri(meta-sulphophenyl)-phosphine.

8. A process according to claim 1, wherein the operation is performed in the presence of an organic solvent which dissolves said unsaturated aldehyde.

9. A process according to claim 8, wherein the organic solvent is an alcohol, ether, ketone, ester used individually or as a mixture.

10. A process according to claim 1 wherein the hydrogenation is performed at a temperature of from 10 to 100° C.

11. A process according to claim 1 wherein the hydrogenation is performed at a pressure of from 10 to 50 bars.

12. A process according to claim 8, wherein the organic solvent is a halogenated aliphatic or aromatic hydrocarbon used individually or as a mixture.

* * * * *